United States Patent
Oyama et al.

(10) Patent No.: US 12,171,846 B2
(45) Date of Patent: Dec. 24, 2024

(54) NONWOVEN FABRIC FOR SKIN CARE PRODUCTS, FACE MASK, AND CLEANSING SHEET

(71) Applicant: Toray Industries, Inc., Tokyo (JP)

(72) Inventors: Kumi Oyama, Otsu (JP); Hiroshi Kajiyama, Otsu (JP); Makoto Nakahara, Otsu (JP)

(73) Assignee: Toray Industries, Inc., Tokyo (JP)

( * ) Notice: Subject to any disclaimer, the term of this patent is extended or adjusted under 35 U.S.C. 154(b) by 916 days.

(21) Appl. No.: 17/280,530

(22) PCT Filed: Sep. 26, 2019

(86) PCT No.: PCT/JP2019/037824
§ 371 (c)(1),
(2) Date: Mar. 26, 2021

(87) PCT Pub. No.: WO2020/071228
PCT Pub. Date: Apr. 9, 2020

(65) Prior Publication Data
US 2022/0040050 A1 Feb. 10, 2022

(30) Foreign Application Priority Data
Oct. 2, 2018 (JP) ................................ 2018-187161

(51) Int. Cl.
| | | |
|---|---|---|
| A61K 8/02 | (2006.01) | |
| A45D 44/00 | (2006.01) | |
| A61K 8/73 | (2006.01) | |
| A61K 8/88 | (2006.01) | |
| A61Q 19/10 | (2006.01) | |
| D04H 1/4258 | (2012.01) | |
| D04H 1/4334 | (2012.01) | |
| D04H 1/4382 | (2012.01) | |
| D04H 1/492 | (2012.01) | |
| B82Y 40/00 | (2011.01) | |

(52) U.S. Cl.
CPC .............. *A61K 8/0212* (2013.01); *A61K 8/73* (2013.01); *A61K 8/88* (2013.01); *A61Q 19/10* (2013.01); *D04H 1/4334* (2013.01); *D04H 1/4383* (2020.05); *D04H 1/43835* (2020.05); *D04H 1/43838* (2020.05); *D04H 1/492* (2013.01); *B82Y 40/00* (2013.01); *D10B 2201/24* (2013.01); *D10B 2331/02* (2013.01)

(58) Field of Classification Search
None
See application file for complete search history.

(56) References Cited

U.S. PATENT DOCUMENTS

| | | |
|---|---|---|
| 7,094,462 B1 | 8/2006 | Yokoyama et al. |
| 7,569,534 B2 | 8/2009 | Nonomura et al. |
| 9,428,851 B2 | 8/2016 | Masuda et al. |
| 2007/0219107 A1 | 9/2007 | Nonomura et al. |
| 2008/0269095 A1 | 10/2008 | Aubrun-Sonneville |
| 2020/0170382 A1 | 6/2020 | Oyama et al. |

FOREIGN PATENT DOCUMENTS

| | | | |
|---|---|---|---|
| CA | 949737 A | 6/1974 | |
| CN | 1160502 C | 8/2004 | |
| CN | 104487629 A | 4/2015 | |
| CN | 106133226 A | 11/2016 | |
| EP | 0870496 A2 | 10/1998 | |
| EP | 3643825 A1 | 4/2020 | |
| JP | 2006045096 A | 2/2006 | |
| JP | 2009097121 A | 5/2009 | |
| JP | 2011006807 A | 1/2011 | |
| JP | 2012223396 A | 11/2012 | |
| JP | 2013209337 A | 10/2013 | |
| JP | 2013240432 A | 12/2013 | |
| JP | 2015148023 A | 8/2015 | |
| KR | 20170045309 A * | 4/2017 | ........... A61K 8/0208 |
| TW | M447138 U | 2/2013 | |
| WO | 2012173116 A1 | 12/2012 | |
| WO | 2014045680 A1 | 3/2014 | |
| WO | 2018235859 A1 | 12/2018 | |

OTHER PUBLICATIONS

Li et al. Primarily industrialized trial of novel fibers spun from cellulose dope in NaOH/urea aqueous solution. Ind. Eng. Chem. Res. 2010, 49, 11380-11384. (Year: 2010).*
International Search Report and Written Opinion for International Application No. PCT/JP2019/037824, dated Dec. 3, 2019, 5 pages.
Chinese Office Action for Chinese Application No. 201980060187. 5, dated May 7, 2022 with translation, 14 pages.
Extended European Search Report for European Application No. 19869314.5, dated Jun. 3, 2022, 7 pages.
Maruzen, Inc., "Textile Encyclopedia," Mar. 25, 2002, with Concise Statement of Relevance, 3 pages.
Taiwanese Office Action for Taiwanese Application No. 108135479, dated Sep. 12, 2023 with translation, 14 pages.

* cited by examiner

*Primary Examiner* — Lakshmi S Channavajjala
(74) *Attorney, Agent, or Firm* — Buchanan Ingersoll & Rooney PC

(57) ABSTRACT

Provided is a nonwoven fabric for skin care products. The nonwoven fabric includes: a thermoplastic resin fiber having a single fiber diameter of 50 nm or more and 800 nm or less; and a cellulose fiber. A tensile strength of the cellulose fiber measured in accordance with JIS L 1015:2010 8.7.2 is 1.9 cN/dtex or less, a total content of the thermoplastic resin fiber and the cellulose fiber is 85% by mass or more relative to a total mass of the nonwoven fabric for skin care products, a content ratio by mass of the thermoplastic resin fiber and the cellulose fiber (thermoplastic resin fiber/cellulose fiber) is 0.23 to 1.50, and a density of the nonwoven fabric for skin care products is 0.08 g/cm$^3$ to 0.16 g/cm$^3$.

7 Claims, No Drawings

NONWOVEN FABRIC FOR SKIN CARE PRODUCTS, FACE MASK, AND CLEANSING SHEET

CROSS REFERENCE TO RELATED APPLICATIONS

This is the U.S. National Phase application of PCT/JP2019/037824 filed Sep. 26, 2019, which claims priority to Japanese Patent Application No. 2018-187161, filed Oct. 2, 2018, the disclosures of these applications being incorporated herein by reference in their entireties for all purposes.

FIELD OF THE INVENTION

The present invention relates to a nonwoven fabric for skin care products, a face mask, and a cleansing sheet.

BACKGROUND OF THE INVENTION

Sheet-like skin care cosmetics represented by face masks and cleansing sheets are used for various purposes such as penetration of a medicinal solution into a skin and removal of cosmetics. The face mask can retain the medicinal solution on the surface of skin for a certain period of time and thus allows the medicinal solution to be sufficiently penetrated into the skin as compared with conventional skin care products applied directly to the skin. In addition, the cleansing sheet provides a high cleansing effect due to both removal of the cosmetic by a cleansing agent and removal effect by the contact of the sheet with the skin. Due to the above-described excellent performance, various commercial products have been developed as the sheet-like skin care products.

Recently, it has been known that a nonwoven fabric including fibers made of a thermoplastic resin having a single fiber diameter of 1 nm to 500 nm and a fiber having a tensile strength at the time of a wet state of 2.0 cN/dtex or more is formed, whereby a product obtained by immersing this nonwoven fabric into a cleansing agent has excellent strength at the time of a wet state and, in addition, improved adhesion to a skin and wipeability of a cosmetic attached to skin (Patent Literature 1).

Patent Literature

Patent Literature 1: Japanese Patent Application Laid-open No. 2009-97121

SUMMARY OF THE INVENTION

The nonwoven fabric disclosed in Patent Literature 1 (hereinafter, referred to as the known nonwoven fabric 1) described above includes 30% by mass to 70% by mass of a fiber having a high tensile strength at the time of a wet state of 2.0 cN/dtex or more. Thus, although the skin care product obtained by impregnating the known nonwoven fabric 1 into a cleansing agent or a cosmetic has excellent strength at the time of a wet state, the skin care product has problems of insufficient adhesion to skin (in particular, adhesion when a certain time has passed after use of the skin care product) and wipeability of the cosmetics attached to the skin.

Therefore, in view of the above-described problems, an object of the present invention is to provide a nonwoven fabric for skin care products having excellent handleability when a skin care product is made and having excellent adhesion to skin and wipeability of cosmetic attached to skin when the skin care product is made.

In order to solve the above-described problem, the present invention includes the following constitutions. Namely:

(1) A nonwoven fabric for skin care products includes a thermoplastic resin fiber having a single fiber diameter of 50 nm or more and 800 nm or less, and a cellulose fiber. A tensile strength of the cellulose fiber measured in accordance with JIS L 1015:2010 8.7.2 is 1.9 cN/dtex or less, a total content of the thermoplastic resin fiber and the cellulose fiber is 85% by mass or more relative to a total mass of the nonwoven fabric for skin care products, a content ratio by mass of the thermoplastic resin fiber and the cellulose fiber (thermoplastic resin fiber/cellulose fiber) is 0.23 to 1.50, and a density of the nonwoven fabric for skin care products is 0.08 g/cm$^3$ to 0.16 g/cm$^3$;

(2) In the nonwoven fabric for skin care products of (1), the thermoplastic resin fiber is a polyamide fiber;

(3) In the nonwoven fabric for skin care products of (1) or (2), the cellulose fiber is rayon;

(4) In the nonwoven fabric for skin care products of any one of (1) to (3), a fiber length of the cellulose fiber is 35 mm or more;

(5) In the nonwoven fabric for skin care products of any one of (1) to (4), the density is 0.08 g/cm$^3$ to 0.14 g/cm$^3$;

(6) A face mask includes the nonwoven fabric for skin care products of any one of (1) to (5); and (7) A cleansing sheet includes the nonwoven fabric for skin care products of any one of (1) to (5).

According to the present invention, the nonwoven fabric for skin care products having excellent handleability when a skin care product is made and having excellent adhesion to skin and wipeability of cosmetics attached to skin when the skin care product is made by forming the nonwoven fabric for skincare products, in which the nonwoven fabric for skincare products includes the specific thermoplastic resin fiber and the specific cellulose fiber and, furthermore, in which the total content of the thermoplastic resin fiber and the cellulose fiber and the content ratio by mass of the thermoplastic resin fiber to the cellulose fiber (Thermoplastic resin fiber/Cellulose fiber) are in the specific ranges.

DETAILED DESCRIPTION OF EMBODIMENTS OF THE INVENTION

Hereinafter, the embodiments of the nonwoven fabric for skin care products according to the present invention will be described in detail. The nonwoven fabric for skin care products according to the present invention includes a thermoplastic resin fiber having a single fiber diameter of 50 nm or more and 800 nm or less and a cellulose fiber having a tensile strength of 1.9 cN/dtex or less measured in accordance with JIS L 1015: 2010 8.7.2. In addition, in the nonwoven fabric for skin care products according to the present invention, a total content of the thermoplastic resin fiber and the cellulose fiber is 85% by mass or more, a content ratio by mass of the thermoplastic resin fiber to the cellulose fiber (Thermoplastic resin fiber/Cellulose fiber) is 0.23 to 1.50, and a density is 0.08 g/cm$^3$ to 0.16 g/cm$^3$. Hereinafter, the tensile strength measured in accordance with JIS L 1015: 2010 8.7.2 may be simply referred to as the tensile strength. The total content of the thermoplastic resin fiber and the cellulose fiber may be simply referred to as the total content. The content ratio by mass of the thermoplastic resin fiber to the cellulose fiber (Thermoplastic resin fiber/Cellulose fiber) may be simply referred to as the content ratio by mass.

The nonwoven fabric for skin care products according to the present invention exhibits an excellent static coefficient of friction, followability, a liquid retention property, and softness at compression by employing the above-described constitution. The detail of the mechanism in which the nonwoven fabric for skin care products according to the present invention exhibits the above-described effect is presumed as follows. Namely, the nonwoven fabric for skin care products according to the present invention includes the thermoplastic resin fiber having a single fiber diameter of 50 nm or more and 800 nm or less, in which the single fiber diameter is extremely thin and thus the thermoplastic rein fiber has excellent softness, and among the cellulose fibers that tend to have an excellent water absorption property and a high tensile strength, the cellulose fiber having a tensile strength of 1.9 cN/dtex or less, which provides adequate softness. At the same time, a large part of the nonwoven fabric for skin care products is constituted of the thermoplastic resin fiber and the cellulose fiber. In addition, the content ratio by mass of the two fibers having different properties is in a specific range of 0.23 to 1.50 and the density is limited to 0.08 g/cm$^3$ to 0.16 g/cm$^3$ in the above-described range of the content ratio by mass. Consequently, the nonwoven fabric for skin care products according to the present invention provides excellent handleability of the skin care products in which the nonwoven fabric for skin care products is used and also has excellent softness at the time of a wet state (that is, softness at compression), followability, and a liquid retention property. These properties allow the skin care product using the nonwoven fabric for skin care products according to the present invention (hereinafter, may be referred to as the present skin care product) to exhibit excellent followability to unevenness existing on the surface of a user's skin (hereinafter, may be simply referred to as the skin) and generation of a large gap between the present skin care product and the skin to be reduced in the time of use. Furthermore, the nonwoven fabric for skin care products according to the present invention includes the thermoplastic resin fiber, which is an extremely thin fiber, in a specific amount. Therefore, the thermoplastic resin fiber existing on the surface of the nonwoven fabric for skin care products goes into small winkles existing on the skin at the time of use of the present skin care product and thus the contact area of the nonwoven fabric for skin care products and the skin becomes larger, resulting in providing an excellent static coefficient of friction. Thus, the present skin care product does not easily slip on the skin. Therefore, it is presumed that the excellent adhesion and excellent wipeability of the present skin care product are exhibited by the excellent followability of the present skin care product to the skin and the reduction in slippage between the present skin care product and the skin.

In addition, the density of the nonwoven fabric for skin care products according to the present invention is in a range of 0.08 g/cm$^3$ to 0.16 g/cm$^3$. This allows handleability to be excellent even in the nonwoven fabric for skin care products according to the present invention (that is, the nonwoven fabric for skin care products including the thermoplastic resin fiber that is extremely thin and has excellent softness in a relatively high content) having a total content of the thermoplastic fiber and the cellulose fiber of 85% by mass or more relative to the total mass of the nonwoven fabric for skin care products and, in addition, a content ratio by mass of the thermoplastic resin fiber and the cellulose fiber (Thermoplastic resin fiber/Cellulose fiber) of 0.23 to 1.50. Consequently, the skin care product using the nonwoven fabric for skin care products according to the present invention provides all of the handleability, adhesion, and wipeability in high level and, in addition, provides excellent followability and softness at the time of a wet state.

In addition, the skin care product using the nonwoven fabric for skin care products according to the present invention has not only excellent adhesion with the skin immediately after the use of the skin care product but also excellent adhesion with the skin at a certain period of time after starting to use the skin care product. Whether the adhesion of the skin care product to the skin at a certain period of time after starting to use is excellent can be evaluated by the adhesion to the skin 20 minutes after starting to use the skin care product (hereinafter, may be simply referred to as adhesion after 20 minutes).

The nonwoven fabric for skin care products of the present invention includes the thermoplastic resin fiber having a single fiber diameter of 50 nm or more and 800 nm or less. First, this thermoplastic resin fiber will be described.

The thermoplastic resin fiber used for the nonwoven fabric for skin care products according to the present invention is a fiber having a single fiber diameter of 50 nm or more and 800 nm or less. The nonwoven fabric for skin care products including the thermoplastic resin fiber determining the single fiber diameter of the thermoplastic resin fiber to be 50 nm or more allows the thermoplastic resin fiber to be prevented from falling off and remaining on the skin when the skin care product using the nonwoven fabric for skin care products is used. On the other hand, the nonwoven fabric for skin care products including the thermoplastic resin fiber determining the single fiber diameter of the thermoplastic resin fiber to be 800 nm or less allows the contact area of the surface of the nonwoven fabric for skin care products with the skin to increase and the coefficient of friction between the skin and the nonwoven fabric for skin care products to be improved. Consequently, the nonwoven fabric is prevented from slipping on the skin surface and thus the adhesion and wipeability of the skin care product using this nonwoven fabric for skin care products are excellent. From the above-described reasons, the upper limit of the single fiber diameter of the thermoplastic resin fiber is more preferably 600 nm or less and further preferably 300 nm or less.

Examples of the thermoplastic resin included in the thermoplastic resin fiber used in the present invention include polyesters, polyamides, and polyolefins. Of these thermoplastic resins, the thermoplastic resin fiber is preferably a polyamide fiber from the viewpoint of improving the adhesion and wipeability at the time of a wet state. Use of the polyamide fiber, which has a water absorption property, as a thermoplastic resin fiber having a single fiber diameter of 50 nm or more and 800 nm or less allows the capillary effect of absorbing a medicinal solution existing between the nonwoven fabric for skin care products and the skin to be improved and the nonwoven fabric for skin care products to absorb the excess medicinal solution between the nonwoven fabric and the skin. Consequently, the contact area between the nonwoven fabric for skin care products and the skin increases and, as a result, the adhesion and wipeability at the time of a wet state can be further improved. Here, in these thermoplastic resins, other components may be polymerized or additives such as a stabilizer may be contained.

Here, as the polyamide, for example, nylon 6, nylon 11, nylon 12, nylon 66, and various aramid resins can be used. Of these polyamides, nylon 6 having an excellent water absorption property is preferably used.

In the group of thermoplastic resin fibers included in the present invention, each thermoplastic resin fiber may be dispersed and present individually, at least a part of the thermoplastic resin fiber is partially bonded to each other to be present, or at least a part of the thermoplastic resin fiber may be present by agglomerating the thermoplastic resin fibers to form of a bundle. Furthermore, the thermoplastic resin fiber is not particularly limited in its length, sectional shape, or the like and may be in the form of what is called fiber-like shape.

In addition, the nonwoven fabric for skin care products according to the present invention includes the cellulose fiber having a tensile strength of 1.9 cN/dtex or less, which has moderate softness. Hereinafter, this cellulose fiber will be described.

The nonwoven fabric for skin care products in a wet state has higher followability to the fine unevenness of the skin. As a result, the tensile strength of the cellulose fiber is preferably 1.7 cN/dtex or less and more preferably 1.5 cN/dtex or less because the adhesion and wipeability of the skin care product using the nonwoven fabric for skin care products are more improved. The lower limit of the tensile strength of the cellulose fiber is not particularly limited and is preferably 0.9 cN/dtex or more because the handleability of the present skin care product can be more improved. In addition, the fiber length of a cellulose fiber is preferably 35 mm or more. The cellulose fiber having a fiber length of 35 mm or more allows the degree of entanglement among the fibers in the nonwoven fabric for skin care products to increase. The increase in the degree of entanglement among the fibers in the nonwoven fabric for skin care products results in increasing the strength of the nonwoven fabric for skin care products at the time of a wet state. As a result, the handleability of the present skin care product becomes more excellent. The upper limit of the fiber length of the cellulose fiber is not particularly limited and is preferably 80 mm or less from the viewpoint that the process passability of the fiber in the production process described below becomes more excellent.

As the cellulose fiber used in the present invention, plant-based natural fibers such as pulp and cotton, regenerated fibers such as rayon and cupra, and semi-synthetic fibers such as acetate and triacetate can be used. Of these cellulose fibers, rayon is preferable because the adhesion and wipeability of the present skin care product can be more excellent.

In the nonwoven fabric for skin care products according to the present invention, the total content of the thermoplastic resin fiber and the cellulose fiber is 85% by mass or more relative to the total mass. It is presumed that the nonwoven fabric for skin care products having a total content of 85% by mass or more of the fibers allows the softness of the nonwoven fabric for skin care products to be improved due to exhibiting the effect of the thermoplastic resin fiber having excellent softness and the cellulose fiber also having excellent softness and thus that the present skin care product has excellent adhesion and wipeability. From the above-described reasons, the total content is preferably 95% by mass or more and more preferably 100% by mass.

In the nonwoven fabric for skin care products according to the present invention, the content ratio by mass of thermoplastic resin fiber to cellulose fiber (Thermoplastic resin fiber/Cellulose fiber) is 0.23 to 1.50. As described above, the nonwoven fabric for skin care products has the content ratio by mass within the above-described range and consequently the adhesion and wipeability of the present skin care product are improved.

Here, the softness in the present invention refers to softness when the nonwoven fabric for skin care products according to the present invention is compressed in the thickness direction of the nonwoven fabric for skin care products (that is, softness at compression). As a method of evaluating the above-described softness, there is a WC value measured by a KES compression tester. The above-described WC value is the amount of work (gf·cm/cm$^2$) up to the maximum pressure when a fabric is compressed. As this value becomes higher, the softness at compression becomes better. The WC value measured by the KES compression test in the present invention is a WC value measured at the time of a wet state and, the WC value of the nonwoven fabric for skin care products of the present invention is preferably 0.40 gf·cm/cm$^2$ or more, more preferably 0.50 gf·cm/cm$^2$ or more, and further preferably 0.60 gf·cm/cm$^2$ or more.

The nonwoven fabric for skin care products of the present invention may be a nonwoven fabric for skin care products including a thermoplastic resin fiber having a single fiber diameter of more than 800 nm, a cellulose fiber having a tensile strength at the time of a wet state of more than 1.9 cN/dtex, and fibers other than the thermoplastic resin fiber and the cellulose fiber in the range where the effect is not impaired. Examples of fibers other than the thermoplastic resin fiber and the cellulose fiber include animal natural fibers such as silk and wool. Furthermore, for example, in the case where the thermoplastic resin fiber having a diameter of more than 800 nm includes a polyethylene terephthalate fiber having a single fiber fineness of 1.6 dtex or more (single fiber diameter 12.3 μm), the sectional shape of this fiber is preferably an atypical section and more preferably a flat section. It is presumed that the fiber having a sectional shape of the atypical section or the flat section has smaller second moment of the fiber than that of the fiber having the circular section and consequently that the softness of the nonwoven fabric for skin care products (that is, the softness at compression) and followability at the time of a wet state are improved.

The basis weight of the nonwoven fabric for skin care products according to the present invention is preferably 25 g/m$^2$ to 150 g/m$^2$ and the lower limit thereof is more preferably 30 g/m$^2$ or more, and further preferably 40 g/m$^2$ or more. On the other hand, the upper limit thereof is more preferably 100 g/m$^2$ or less, and further preferably 70 g/m$^2$ or less. The nonwoven fabric for skin care products having a basis weight of 25 g/m$^2$ or more allows the strength of the nonwoven fabric for skin care products to be excellent. On the other hand, the nonwoven fabric for skin care products having a basis weight of 150 g/m$^2$ or less allows the flexibility of the nonwoven fabric to be improved. Here, the basis weight of the nonwoven fabric for skin care products according to the present invention can be measured in accordance with JIS L 1913:1998 6.2.

The density of the nonwoven fabric for skin care products according to the present invention is 0.08 g/cm$^3$ to 0.16 g/cm$^3$. The lower limit thereof is preferably 0.09 g/cm$^3$ or more and further preferably 0.10 g/cm$^3$ or more. On the other hand, the upper limit thereof is preferably 0.15 g/cm$^3$ or less and further preferably 0.14 g/cm$^3$ or less. Setting the density to 0.08 g/cm$^3$ or more allows the handleability of the skin care product to be improved even in the case where the thermoplastic resin fiber having a single fiber diameter of 50 nm or more and 800 nm or less, in which the single fiber diameter is extremely thin and thus the thermoplastic rein fiber has excellent softness is included in a high content. On the other hand, setting the density to 0.16 g/cm$^3$ or less allows the followability and softness at the time of a wet state to be provided. Here, the density of the nonwoven fabric for skin care products according to the present invention can be determined by measuring the thickness of the nonwoven fabric for skin care products in accordance with JIS L1913:1998 6.1.2 Method A and in accordance with the following formula using the above-described basis weight and the above-described thickness.

Density $(g/cm^3)$=Basis weight $(g/m^2)$/Thickness (mm)/1,000

The nonwoven fabric for skin care products of the present invention includes the thermoplastic resin fiber having a single fiber diameter of 50 nm or more and 800 nm or less. It is presumed that the thermoplastic resin fiber goes into the fine unevenness on the skin surface, whereby the contact area between the skin and the nonwoven fabric for skin care products increases, the coefficient of friction between the nonwoven fabric for skin care products and the skin is improved, slip of the nonwoven fabric for skin care products on the surface of the skin is reduced, and consequently the thermoplastic resin fiber contributes to the improvement of the adhesion and wipeability of the present skin care product. From the viewpoint described above, the nonwoven fabric for skin care products according to the present invention preferably includes the thermoplastic resin fiber in a content of 20% by mass or more and further preferably 30% by mass or more relative to the total mass of the nonwoven fabric for skin care products. Here, the coefficient of friction between the nonwoven fabric for skin care products and the skin can be evaluated by the static coefficient of friction when the nonwoven fabric for skin care products is impregnated with a lotion in accordance with the inclination method in JIS P 8147:1994 3.2. The static coefficient of friction between the nonwoven fabric for skin care products and the skin is preferably 0.50 or more, more preferably 0.60 or more, and further preferably 0.70 or more because the adhesion and wipeability of the present skin care product become more excellent.

In addition, it is presumed that the nonwoven fabric for skin care products according to the present invention includes the cellulose fiber having a tensile strength of 1.9 cN/dtex or less, whereby the nonwoven fabric for skin care products follows the fine unevenness of the skin at the time of a wet state to improve the followability of the nonwoven fabric for skin care products and consequently the cellulose fiber contributes to the improvement of the adhesion and wipeability of the present skin care product. In other words, the 20% elongation stress of the nonwoven fabric for skin care products at the time of a wet state is preferably 5.0 N/25 mm or less because the above-described followability is sufficient for improving the adhesion and the like of the present skin care product. From the above-described reasons, the 20% elongation stress is more preferably 4.0 N/25 mm or less and further preferably 3.0 N/25 mm or less. The elongation stress of the nonwoven fabric for skin care products according to the present invention at the time of a wet state can be measured by reading out the stress when the nonwoven fabric for skin care products is elongated at 20% of the initial length with a constant speed elongation type tensile tester in accordance with JIS L 1913:1998 6.3.2. In addition, for example, appropriate adjustment of the content and the single fiber fineness of the cellulose fiber included in the nonwoven fabric for skin care products according to the present invention allows 20% elongation stress of the nonwoven fabric for skin care products at the time of a wet state to be desired stress.

The nonwoven fabric for skin care products according to the present invention preferably includes the cellulose fiber, which has an excellent liquid retention property, in a content of 35% by mass or more relative to the total mass of the nonwoven fabric for skin care products. When the skin care product is prepared by impregnating a medicinal solution into the nonwoven fabric for skin care products, such a constitution allows the volatilization of the medicinal solution into air to be reduced because the cellulose fiber takes the medicinal solution inside the fiber. Consequently, the liquid retention property of the present skin care product is improved. It is presumed that this liquid retention property improvement contributes to improvement in the adhesion (in particular, the adhesion after 20 minutes) and wipeability of the present skin care product. As a method for evaluating the above-described liquid retention property, the liquid retention property can be evaluated by a medicinal solution retention ratio using the value of the initial amount of the lotion that the nonwoven fabric for skin care products holds and the value of the amount of the lotion that the nonwoven fabric for skin care products holds after 20 minutes when the nonwoven fabric for skin care products impregnated with the lotion is placed on pseudo-skin. The medicinal solution retention ratio after 20 minutes of the nonwoven fabric for skin care products is preferably 75% or more, more preferably 80% or more, and further preferably 85% or more because the adhesion and wipeability at the time of a wet state are retained for a long period of time.

Here, the nonwoven fabric for skin care products according to the present invention is preferably a dry nonwoven fabric. Use of the dry nonwoven fabric allows the thickness of the nonwoven fabric to be increased as compared with a wet nonwoven fabric, and, as a result, the softness of the nonwoven fabric at compression can be improved. Furthermore, among the dry nonwoven fabrics, the nonwoven fabric for skin care products according to the present invention is preferably a spunlace nonwoven fabric. The spunlace nonwoven fabric can be obtained by a method in which constituent fiber is entangled by high-pressure water flow. Compared with a method in which a constituent fiber is entangled by needle punch, this method provides the nonwoven fabric for skin care products having low breakage of the constituent fiber at the time of entanglement and having flexible feeling.

As a method for obtaining the thermoplastic resin fiber according to the present invention, for example, the method disclosed in WO 2012/173116 pamphlet can be employed.

Skin care products such as face masks or skin care sheets, eye masks, cleansing sheets, and cleansing sheets for point makeup can be prepared from the nonwoven fabric for skin care products according to the present invention by immersing the nonwoven fabric for skin care products into a medicinal solution such as a lotion, an essence, or a cleansing agent.

EXAMPLES

The measuring method used in Examples will be described below.

(1) Tensile Strength of Cellulose Fiber

The tensile strength of cellulose fiber was measured in accordance with JIS L 1015:2010 8.7.2.

Specifically, 50 cellulose fibers were collected from the nonwoven fabric for skin care products. Subsequently, each fiber was immersed in water for 2 minutes and thereafter one of 50 cellulose fibers was attached to a constant speed elongation type tensile tester to measure the tensile strength in water. This measurement was carried out for 50 cellulose fibers. The clamping distance was 20 mm. Load was applied at a tensile speed of 20 mm/min until the sample was cut and the strength at the time of the cut was measured. The average value of the measurement results of 50 tensile strength measurements was calculated. The calculated value was determined to be the tensile strength of the cellulose fiber. In the case where the fiber was too short to test with a clamping distance of 20 mm, load was applied until the sample was cut at a tension speed of 10 mm/min with a clamping distance of 10 mm and the strength at the time of cut was measured.

(2) Fiber Length of Cellulose Fiber

The fiber length of the cellulose fiber was measured in accordance with the direct method (Method C) in JIS L 1015:2010 8.4.1. Specifically, the nonwoven fabric for skin care products having a size of 80 mm×80 mm was prepared as a sample. On one side of the sample, a center point and a circle having a diameter of 6 cm sharing the center point of this sample were drawn. Subsequently, one cellulose fiber was randomly taken out at the time from the inside of this circle. A total of 25 cellulose fibers were collected. The same operation as this operation was also carried out on the other side of this sample. The fiber lengths of the total of 50 cellulose fibers obtained from this sample were measured as follows.

One cellulose fiber taken out randomly was straightened without elongation. Subsequently, the fiber length of the cellulose fiber in the straightened state was measured to the mm unit on a scale. This measurement was carried out for 50 cellulose fibers and the average value of the measured values of 50 fibers was calculated. The average value was determined to be the fiber length.

(3) Basis Weight

The basis weight was measured in accordance with JIS L 1913:1998 6.2. Specifically, three 50 mm×50 mm test specimens were collected from the sample of the nonwoven fabric for skin care products using a steel ruler and a razor blade. The mass of the test specimen in the standard state was measured and the mass per unit area was determined by the following equation, followed by calculating the average value.

$$ms = m/S$$

ms: Mass per unit area (g/m$^2$)

m: Average mass of test specimen (g)

S: Area of test specimen (m$^2$).

(4) Thickness

The thickness was measured in accordance with JIS L1913:1998 6.1.2 Method A. Five 50 mm×50 mm test specimens were collected from the sample of the nonwoven fabric for skin care products using a steel ruler and a razor blade. The thickness was measured using a thickness measurement instrument (Constant Pressure Thickness Measurement Instrument Type PG11J, manufactured by TECLOCK Co., Ltd.) by applying a pressure of 0.36 kPa to the test specimen in the standard state for 10 seconds. The measurement was performed for each of the test specimens (5 test specimens) and the average value was calculated.

(5) Density

The density was determined in accordance with the following formula using the above-described basis weight in (3) and the above-described thickness in (4).

$$\text{Density (g/cm}^3\text{)} = \text{Basis weight (g/m}^2\text{)/Thickness (mm)/1,000}$$

(6) Static Coefficient of Friction

The static coefficient of friction was measured in accordance with the inclination method in JIS P8147:1994 3.2. Specifically, as the test specimens (nonwoven fabric for skin care products) having a width of 30 mm and a length of 130 mm, five specimens in which the direction of the movement of a production apparatus for a nonwoven fabric for skin care products is the length direction and five specimens in which the direction perpendicular to the direction of the movement of the production apparatus for a nonwoven fabric for skin care products is the length direction, that is, 10 test specimens in total were prepared. For the evaluation in the direction of the movement, the test specimen was immersed for 10 minutes in a lotion (manufactured by Ryohin Keikaku Co., Ltd., "Kesyousui/Binkanhadayou Sittori Taipu (Lotion/Moist Type for Sensitive Skin)") and taken out. This test specimen was immediately attached to the weight of a slip inclination angle measurement device. On the other hand, a silicone pseudo-skin (manufactured by Beaulax Co., Ltd.) was attached to the slip inclination angle measurement device. The weight attached with the test specimen was placed on the silicone pseudo-skin so that the measurement surface of the test specimen came into contact with the silicone pseudo-skin and that the direction of the movement (length direction) of the test specimen and the slip direction of the slip inclination angle measurement device were matched. The inclination angle at the time of dropping the weight under the condition of an inclination angle rate of less than 3°/second was read out. The tangent (tan δ) of the inclination angle was determined to be the static coefficient of friction. In addition, for the evaluation in the direction perpendicular to the direction of the movement, the weight attached with the test specimen was placed on the silicone pseudo-skin so that the direction perpendicular to the direction of the movement (length direction) of the test specimen and the slip direction of the slip inclination angle measurement device were matched and that the evaluation was performed in the same manner. The average of the obtained static coefficients of friction of the 10 test specimens was determined to be the static coefficient of friction of the nonwoven fabric for skin care products according to the present invention. In addition, in order to prevent the fluctuation of the measurement value, the lotion used in the above-described measurement shall be within one month after opening and the quasi-skin used in the above-described measurement shall be used 5 times or more and 50 times or less.

(7) Followability (20% Elongation Stress)

The followability was measured in accordance with JIS L 1913:1998 6.3.2. Specifically, as the test specimens (nonwoven fabric for skin care products) having a width of 25 mm and a length of 150 mm, five specimens in which the direction of the movement of the production apparatus for a nonwoven fabric for skin care products is the length direction and five specimens in which the direction perpendicular to the direction of the movement of a production apparatus for a nonwoven fabric for skin care products is the length direction, that is, 10 test specimens in total were prepared. For the evaluation in the direction of the movement, the test specimen was immersed into distilled water at 20° C. for 10 minutes and taken out. This test specimen was immediately attached to a constant speed elongation type tensile tester so that the tensile direction and the direction of the movement (length direction) of the sample specimen were matched. Load was applied under conditions of a clamping distance of 100 mm and a tensile speed of 200 mm/min until the test specimen was cut. The stress when the test specimen was elongated at 20 mm (N/25 mm) was read out from a stress-strain curve and the read value was determined to be 20% tensile stress. In addition, for the evaluation in the direction perpendicular to the direction of the movement, the test specimen was attached to a constant speed elongation type tensile tester so that the tensile direction and the direction perpendicular to the direction of the movement (length direction) of the test specimen were matched and that the evaluation was performed in the same manner. The lower value of the obtained average values of the 20% elongation stress in both of the directions was determined to be the 20% elongation stress of the nonwoven fabric for skin care products.

(8) Liquid Retention Property (Mass Retention Rate of Lotion)

Five test specimens (nonwoven fabrics for skin care products) having a width of 25 mm and a length of 25 mm were collected from a sample in which humidity was conditioned under an atmosphere of a temperature of 20° C. and a humidity of 60% RH for 24 hours. Subsequently, the mass (g) of this test specimen was measured. In addition, the mass (g) of silicone pseudo-skin (manufactured by Beaulax Co., Ltd., size: diameter 50 mm) was measured. The test specimen was placed on this silicone pseudo-skin and a lotion (manufactured by Ryohin Keikaku Co., Ltd., "Kesyousui/Binkanhadayou Sittori Taipu (Lotion/Moist Type for Sensitive Skin)") was dropped onto this test specimen to give a test specimen containing the lotion in a content of 700% by mass relative to the total mass of the test specimen. The initial total mass (g) of the test specimen, the silicone pseudo-skin, and the lotion was measured in this state. Subsequently, the test specimen was placed in a constant temperature and humidity chamber having a temperature of 20° C. and a humidity of 60% RH. After 20 minutes, the above-described sample was taken out, the total mass (g) of the test specimen, the silicone pseudo-skin, and the lotion after 20 minutes was measured and the mass retention ratio of lotion (%) was calculated in accordance with the following formula. The measurement was carried out for 5 test specimens and the average value was calculated.

Initial mass of lotion (g)=Initial total mass (g)−Mass of silicone pseudo-skin (g)−Mass of test specimen (g)

Mass of lotion after 20 minutes=Total mass after 20 minutes (g)—Mass of silicone pseudo-skin (g)—Mass of test specimen (g)

Mass retention ratio of lotion (%)=Mass of lotion after 20 minutes (g)/Mass of initial lotion (g)× 100.

(9) Softness at Compression

Five test specimens having a size of 60 mm×60 mm were collected from the nonwoven fabric for skin care products. The test specimen was immersed into distilled water at 20° C. for 10 minutes and taken out. This test specimen was immediately attached to a KES compression tester (manufactured by Kato Tech Co., Ltd., model: KES-G5) and a WC value (the amount of work (gf·cm/cm$^2$) up to the maximum pressure) during compressing the sample was measured under conditions of a compression rate of 20 μm/sec and a maximum compression load of 4.9 kPa using a pressure plate having an area of 2 cm$^2$ (circle). The average value of the measured WC values was calculated. The calculated value was determined to be the softness at compression of the nonwoven fabric for skin care products.

(10) Monitoring Evaluation

Face Mask

The nonwoven fabric for skin care products obtained by each Example and Comparative Example was punched into a mask shape to prepare a nonwoven fabric for face masks. The nonwoven fabric for face masks were immersed into a lotion (manufactured by Ryohin Keikaku Co., Ltd., "Kesyousui/Binkanhadayou Sittori Taipu (Lotion/Moist Type for Sensitive Skin)") to give face masks containing 700% by mass of the lotion relative to the total mass of the nonwoven fabric for face masks. Subsequently, the adhesion immediately after starting to use, adhesion 20 minutes after starting to use, followability, difficulty in drying, softness at compression of the face mask and handleability of the face mask were evaluated by 10 female evaluators. These properties were evaluated in 10 full marks based on each person's absolute evaluation and evaluated by the following criteria from the average score of 10 female evaluators (the digits after the decimal point was rounded off). As the score becomes higher, the performance of the face mask becomes better.
A: 9 points to 10 points
B: 6 points to 8 points
C: 3 points to 5 points
D: 0 point to 2 points.

Cleansing Sheet

The nonwoven fabric for skin care products obtained by each Example and Comparative Example was cut into a rectangle having a width of 70 mm and a length of 55 mm. This cut nonwoven fabric was immersed into a cleansing agent (KOSE COSMEPORT Corp., "White Cleansing Water") to give a cleansing sheet containing 700% by mass of the cleansing agent relative to the total mass of the cut nonwoven fabric. Subsequently, wipeability of this cleansing sheet to a cosmetic (manufactured by Shiseido Company, Limited, "BENEFIQUE THEOTY SMART LIQUID EYELINER®") attached to an eye line and handleability of the nonwoven fabric were evaluated by 10 female evaluators. These properties were evaluated in 10 full marks based on each person's absolute evaluation and evaluated by the following criteria from the average score of 10 female evaluators (the digits after the decimal point was rounded off). As the score becomes higher, the performance of the cleansing sheet becomes better.
A: 9 points to 10 points
B: 6 points to 8 points
C: 3 points to 5 points
D: 0 point to 2 points.

(11) Comprehensive Evaluation

The comprehensive evaluation of the feeling of use of the face mask and cleansing sheet made of the nonwoven fabric for skin care products obtained in each Example and Comparative Example was carried out by the 10 female evaluators carrying out the monitoring evaluation of the above (10). The comprehensive evaluation was evaluated in 10 full marks based on each person's absolute evaluation and evaluated by the following criteria from the average score of 10 female evaluators (the digits after the decimal point was rounded off). As the point becomes higher, the performance of the face mask and cleansing sheet becomes better.
A: 9 points to 10 points
B: 6 points to 8 points
C: 3 points to 5 points
D: 0 point to 2 points.

Example 1

Thermoplastic Resin Fiber

Sea-Island Structure Composite Fiber

Polyethylene terephthalate (PET, melt viscosity: 160 Pa·s) serving as an island component and PET (copolymerized PET, melt viscosity: 95 Pa·s) copolymerized with 8.0% by mole of sodium 5-sulfoisophthalate serving as a sea component were separately melted at 290° C. and thereafter weighed. Melt spinning was carried out by flowing these polymers into a pack for spinning in which the known compound spinneret (a compound spinneret having an arrangement disclosed in FIG. 6(b) in WO 2012/173116 pamphlet) was incorporated and a distribution plate having 1,000 drilled distribution holes for the island component per discharge hole was used so that the composition ratio of the island component/sea component was 60/40 and discharging the composite polymer flow from discharge holes to give an unstretched fiber. The unstretched fiber was stretched at a stretching speed of 800 m/min to give a sea-island structure composite fiber having an island component diameter of 230 nm and a structure of 150 dtex-15 filaments. The obtained sea-island structure composite fiber exhibited excellent properties of a strength of 3.6 cN/dtex and an elongation of 30%.

Crimp and Cut Process

The filament made of the above-described sea-island structure composite fiber was crimped (12 threads/25 mm) and thereafter cut into a short fiber having a length of 51 mm to give a thermoplastic resin fiber.

Nonwoven Fabric for Skin Care Products

After 52% by mass of the above-described thermoplastic resin fiber (island component diameter: 230 nm) and 48% by mass of a rayon fiber (single fiber fineness: 1.4 dtex, strength at the time of a wet state: 1.1 cN/dtex, and fiber length: 38 mm) were mixed and opened by a carding machine, web was formed by a cross-lap webber. The web was entangled by high pressure water flow under conditions of a pressure of 10 MPa and a flow rate of 1.0 m/min and dried at a drying temperature of 100° C. using a pin tenter to give a nonwoven fabric. The sea component was removed by treating the nonwoven fabric with a 1% sodium hydroxide aqueous solution under conditions of a temperature of 95° C., a bath ratio of 1:40, and a treatment time of 30 minutes to give 65 g/m² of Nonwoven fabric for skin care products 1 including 30% by mass of the thermoplastic resin fiber (single fiber diameter: 230 nm) and 70% by mass of the rayon fiber (single fiber fineness: 1.4 dtex, strength at the time of a wet state: 1.1 cN/dtex, and fiber length: 38 mm). Here, the content of the thermoplastic resin fiber and the content of the rayon fiber included in above-described Nonwoven fabric for skin care products 1 are the contents relative to the total mass of the above-described nonwoven fabric for skin care products after removing the sea component.

Furthermore, this Nonwoven fabric for skin care products 1 was punched into a mask shape to give face masks. Other than the face masks, this nonwoven fabric for skin care products was cut into a rectangle having a width of 70 mm and a length of 55 mm to give cleansing sheets. The above-described evaluation was performed with respect to the obtained face masks and cleansing sheets. The constitutions and evaluation results of Nonwoven fabric for skin care products 1 are listed in Tables 1 and 2.

Example 2

Thermoplastic Resin Fiber

Polymer Alloy Fiber

Nylon 6 (N6) (40% by mass) having a melt viscosity of 212 Pa·s (262° C., shear rate: 121.6 sec$^{-1}$) and a melting point of 220° C. and poly-L-lactic acid (60% by mass) having a weight average molecular weight of 120,000, a melt viscosity of 30 Pa·s (240° C., shear rate: 2,432 sec$^{-1}$), a melting point of 170° C., and an optical purity of 99.5% or more were separately weighed. These polymers were separately fed to a twin-screw extruding kneader described below in detail and kneaded at 220° C. to give polymer alloy chips.

Screw configuration: Co-rotating fully intermeshing type, double thread screw

Screw: Diameter 37 mm, effective length 1,670 mm, and L/D=45.1

The kneading part length is 28% of the screw effective length.

The kneading part is positioned on the discharge side from ⅓ of the screw effective length.

The screw has 3 back flow parts existing in the course of the screw, and

Vent: Two vents.

The obtained polymer alloy chips were supplied to a single-screw extrusion type melting apparatus serving as a spinning machine for staple. Melt spinning was carried out at a melt temperature of 235° C., a spinning temperature of 235° C. (spinneret surface temperature 220° C.), and a spinning speed of 1,200 m/min to give a polymer alloy fiber. The polymer alloy fiber was combined as a yarn and thereafter the yarn was subjected to steam stretching to give a tow made of the polymer alloy fibers having a single fiber fineness of 3.0 dtex. The obtained polymer alloy fiber exhibited excellent properties of strength of 3.5 cN/dtex, elongation of 45%, and U% of 1.0%.

Crimp and Cut Process

The tow made of the above-described polymer alloy fiber was crimped (12 threads/25 mm) and thereafter cut into a short fiber having a length of 51 mm to give a thermoplastic resin fiber.

Nonwoven Fabric for Skin Care Products

After 52% by mass of the above-described thermoplastic resin fiber (island component diameter: 230 nm), 38% by mass of a rayon fiber (single fiber fineness: 1.4 dtex, strength at the time of a wet state: 1.1 cN/dtex, and fiber length: 38 mm), and 10% by mass of a polyethylene terephthalate (PET) fiber (single fiber fineness: 1.6 dtex) were mixed and opened with a carding machine, web was formed with a cross-lap webber. The web was entangled by high pressure water flow under conditions of a pressure of 10 MPa and a flow rate of 1.0 m/min and dried at a drying temperature of 100° C. using a pin tenter to give a nonwoven fabric. The nonwoven fabric was treated with a 1% sodium hydroxide aqueous solution at a temperature of 95° C., a bath ratio of 1:40, and a treatment time of 30 minutes to remove the sea component to give Nonwoven fabric for skin care products 2 of 65 g/m² including 30% by mass of the thermoplastic resin fiber (single fiber diameter: 230 nm), 55% by mass of the rayon fiber (single fiber fineness: 1.4 dtex, strength at the time of a wet state: 1.1 cN/dtex, and fiber length: 38 mm), and 15% by mass of the polyethylene terephthalate (PET) fiber (single fiber fineness: 1.6 dtex). Here, the content of the thermoplastic resin fiber and the contents of the rayon fiber and the PET fiber included in the above-described nonwoven fabric for skin care products described above are relative to the total mass of the nonwoven fabric for skin care products after removing the sea component.

Furthermore, face masks and cleansing sheets were obtained by the same method as the method in Example 1 using this Nonwoven fabric for skin care products 2. The above-described evaluation was performed with respect to the obtained face masks and cleansing sheets. The constitutions and evaluation results of Nonwoven fabric for skin care products 2 are listed in Tables 1 and 2.

Example 3

Nonwoven fabric for skin care products 3 having a basis weight of 65 g/m² was obtained by the same method as the method in Example 2 except that the PET fiber in Example 2 was replaced by a flat multi-leaf section polyester fiber (single fiber fineness: 1.7 dtex) made of PET.

Subsequently, face masks and cleansing sheets were obtained by the same method as the method in Example 1 using this Nonwoven fabric for skin care products 3. The above-described evaluation was performed with respect to the obtained face masks and cleansing sheets. The constitutions and evaluation results of Nonwoven fabric for skin care products 3 are listed in Tables 1 and 2.

Examples 4

Nonwoven fabric for skin care products 4 having a basis weight of 65 g/m² was obtained by the same method as the method in Example 1 except that nylon 6 (N6 melt viscosity: 190 Pa·s) was used as the island component of the sea-island structure composite fiber in Example 1, that the spinning temperature was changed to 270° C., and that the island component diameter of the sea-island structure composite fiber was changed to 700 nm.

Subsequently, face masks and cleansing sheets were obtained by the same method as the method in Example 1 using this Nonwoven fabric for skin care products 4. The above-described evaluation was performed with respect to the obtained face masks and cleansing sheets. The constitutions and evaluation results of Nonwoven fabric for skin care products 4 are listed in Tables 1 and 2.

Example 5

Nonwoven fabric for skin care products 5 having a basis weight of 65 g/m² was obtained by the same method as the method in Example 4 except that the island component diameter of the sea-island structure composite fiber in Example 4 was changed to 300 nm.

Subsequently, face masks and cleansing sheets were obtained by the same method as the method in Example 1 using this Nonwoven fabric for skin care products 5. The above-described evaluation was performed with respect to the obtained face masks and cleansing sheets. The constitutions and evaluation results of Nonwoven fabric for skin care products 5 are listed in Tables 1 and 2.

Example 6

After 52% by mass of the thermoplastic resin fiber (island component diameter: 230 nm) in Example 2 and 48% by mass of a rayon fiber (single fiber fineness: 1.8 dtex, strength at the time of a wet state: 1.9 cN/dtex, and fiber length: 38 mm) were mixed and opened by a carding machine, web was formed by a cross-lap webber. The web was entangled by high pressure water flow under conditions of a pressure of 10 MPa and a flow rate of 1.0 m/min and dried at a drying temperature of 100° C. using a pin tenter to give a nonwoven fabric. The sea component was removed by treating the nonwoven fabric with a 1% sodium hydroxide aqueous solution under conditions of a temperature of 95° C., a bath ratio of 1:40, and a treatment time of 30 minutes to give Nonwoven fabric for skin care products 6 having a basis weight of 65 g/m² and including 30% by mass of the thermoplastic resin fiber (single fiber diameter: 230 nm) and 70% by mass of the rayon fiber (single fiber fineness: 1.8 dtex, strength at the time of a wet state: 1.9 cN/dtex, and fiber length: 38 mm). Here, the content of the thermoplastic resin fiber and the content of the rayon fiber included in above-described Nonwoven fabric for skin care products 6 are the contents relative to the total mass of the above-described nonwoven fabric for skin care products after removing the sea component.

Subsequently, face masks and cleansing sheets were obtained by the same method as the method in Example 1 using this Nonwoven fabric for skin care products 6. The above-described evaluation was performed with respect to the obtained face masks and cleansing sheets. The constitutions and evaluation results of Nonwoven fabric for skin care products 6 are listed in Tables 1 and 2.

Example 7

Nonwoven fabric for skin care products 7 having a basis weight of 65 g/m² was obtained by the same method as the method in Example 6 except that the rayon fiber (single fiber fineness: 1.8 dtex, strength at the time of a wet state: 1.9 cN/dtex, and fiber length: 38 mm) used in Example 6 was replaced by a rayon fiber (single fiber fineness: 1.6 dtex, strength at the time of a wet state: 1.6 cN/dtex, and fiber length: 38 mm).

Subsequently, face masks and cleansing sheets were obtained by the same method as the method in Example 1 using this Nonwoven fabric for skin care products 7. The above-described evaluation was performed with respect to the obtained face masks and cleansing sheets. The constitutions and evaluation results of Nonwoven fabric for skin care products 7 are listed in Tables 1 and 2.

Example 8

Nonwoven fabric for skin care products 8 having a basis weight of 65 g/m² was obtained by the same method as the method in Example 6 except that the rayon fiber (single fiber fineness: 1.8 dtex, strength at the time of a wet state: 1.9 cN/dtex, and fiber length: 38 mm) used in Example 6 was replaced by a rayon fiber (single fiber fineness: 1.4 dtex, strength at the time of a wet state: 1.1 cN/dtex, and fiber length: 38 mm).

Subsequently, face masks and cleansing sheets were obtained by the same method as the method in Example 1 using this Nonwoven fabric for skin care products 8. The above-described evaluation was performed with respect to the obtained face masks and cleansing sheets. The constitutions and evaluation results of Nonwoven fabric for skin care products 8 are listed in Tables 1 and 2.

Example 9

Nonwoven fabric for skin care products 9 having a basis weight of 65 g/m² was obtained by the same method as the method in Example 8 except that the rayon fiber (single fiber fineness: 1.4 dtex, strength at the time of a wet state: 1.1 cN/dtex, and fiber length: 38 mm) used in Example 8 was replaced by a rayon fiber (single fiber fineness: 1.4 dtex, strength at the time of a wet state: 1.1 cN/dtex, and fiber length: 32 mm).

Subsequently, face masks and cleansing sheets were obtained by the same method as the method in Example 1 using this Nonwoven fabric for skin care products 9. The above-described evaluation was performed with respect to the face masks and the cleansing sheets of this Example. The constitutions and evaluation results of Nonwoven fabric for skin care products 9 are listed in Tables 1 and 2.

Example 10

Thermoplastic Resin Fiber

The tow made of the polymer alloy fiber used in Example 2 was cut to 1 mm and the sea component was removed by treating the cut tow with a 1% sodium hydroxide aqueous solution under conditions of a temperature of 95° C., a bath ratio of 1:40, and a treatment time of 30 minutes to give the short fiber of the thermoplastic resin fiber (single fiber diameter: 230 nm).

Nonwoven Fabric for Skin Care Products

30% by mass of the above-described thermoplastic resin fiber (single fiber diameter: 230 nm) and 70% by mass of a rayon fiber (single fiber fineness: 1.4 dtex, strength at the time of a wet state: 1.1 cN/dtex, and fiber length: 15 mm) were mixed and stirred and thereafter a paper-like product having a basis weight of 65 g/m² was formed with a rectangular sheeting machine and entangled by high pressure water flow by the same method as the method in Example 1 to give Nonwoven fabric for skin care products 10.

Subsequently, face masks and cleansing sheets were obtained by the same method as the method in Example 1 using this nonwoven fabric for skin care products. The above-described evaluation was performed with respect to the obtained face masks and cleansing sheets. The constitutions and evaluation results of Nonwoven fabric for skin care products 10 are listed in Tables 1 and 2.

Example 11

Nonwoven fabric for skin care products 11 having a basis weight of 65 g/m² was obtained by the same method as the method in Example 8 except that the content of the thermoplastic resin fiber (single fiber diameter: 230 nm) used in Example 8 was changed to 20% by mass and that the content of the rayon fiber (single fiber fineness: 1.4 dtex, strength at the time of a wet state: 1.1 cN/dtex, and fiber length: 38 mm) used in Example 8 was changed to 80% by mass.

Subsequently, face masks and cleansing sheets were obtained by the same method as the method in Example 1 using this Nonwoven fabric for skin care products 11. The above-described evaluation was performed with respect to the obtained face masks and cleansing sheets. The constitutions and evaluation results of Nonwoven fabric for skin care products 11 are listed in Tables 3 and 4.

Example 12

Nonwoven fabric for skin care products 12 having a basis weight of 65 g/m² was obtained by the same method as the method in Example 8 except that the content of the thermoplastic resin fiber (single fiber diameter: 230 nm) used in Example 8 was changed to 40% by mass and the content of the rayon fiber (single fiber fineness: 1.4 dtex, strength at the time of a wet state: 1.1 cN/dtex, and fiber length: 38 mm) used in Example 8 was change to 60% by mass.

Subsequently, face masks and cleansing sheets were obtained by the same method as the method in Example 1 using this Nonwoven fabric for skin care products 12. The above-described evaluation was performed with respect to the obtained face masks and cleansing sheets. The constitutions and evaluation results of Nonwoven fabric for skin care products 12 are listed in Tables 3 and 4.

Example 13

Nonwoven fabric for skin care products 13 having a basis weight of 65 g/m² was obtained by the same method as the method in Example 8 except that the content of the thermoplastic resin fiber (single fiber diameter: 230 nm) used in Example 8 was changed to 50% by mass and that the content of the rayon fiber (single fiber fineness: 1.4 dtex, strength at the time of a wet state: 1.1 cN/dtex, and fiber length: 38 mm) used in Example 8 was change to 50% by mass.

Subsequently, face masks and cleansing sheets were obtained by the same method as the method in Example 1 using this Nonwoven fabric for skin care products 13. The above-described evaluation was performed with respect to the obtained face masks and cleansing sheets. The constitutions and evaluation results of Nonwoven fabric for skin care products 13 are listed in Tables 3 and 4.

Example 14

Nonwoven fabric for skin care products 14 having a basis weight of 65 g/m² was obtained by the same method as the method in Example 2 except that the content of the thermoplastic resin fiber (single fiber diameter: 230 nm) used in Example 2 was changed to 50% by mass, that the content of the rayon fiber (single fiber fineness: 1.4 dtex, strength at the time of a wet state: 1.1 cN/dtex, and fiber length: 38 mm) used in Example 2 was change to 35% by mass, and that the content of the PET fiber (single fiber fineness: 1.6 dtex) in Example 2 was changed to 15% by mass.

Subsequently, face masks and cleansing sheets were obtained by the same method as the method in Example 1 using this Nonwoven fabric for skin care products 14. The above-described evaluation was performed with respect to the obtained face masks and cleansing sheets. The constitutions and evaluation results of Nonwoven fabric for skin care products 14 are listed in Tables 3 and 4.

Example 15

Nonwoven fabric for skin care products 15 having a basis weight of 65 g/m² was obtained by the same method as the method in Example 8 except that the pressure of the hydroentanglement was changed to 8 MPa.

Subsequently, face masks and cleansing sheets were obtained by the same method as the method in Example 1 using this Nonwoven fabric for skin care products 15. The above-described evaluation was performed with respect to the obtained face masks and cleansing sheets. The constitutions and evaluation results of Nonwoven fabric for skin care products 15 are listed in Tables 3 and 4.

Example 16

Nonwoven fabric for skin care products 16 having a basis weight of 65 g/m² was obtained by the same method as the method in Example 8 except that the pressure of the hydroentanglement was changed to 15 MPa.

Subsequently, face masks and cleansing sheets were obtained by the same method as the method in Example 1 using this Nonwoven fabric for skin care products 16. The above-described evaluation was performed with respect to the obtained face masks and cleansing sheets. The constitutions and evaluation results of Nonwoven fabric for skin care products 16 are listed in Tables 3 and 4.

Example 17

Nonwoven fabric for skin care products 17 having a basis weight of 65 g/m² was obtained by the same method as the method in Example 4 except that the island component diameter of the sea-island structure composite fiber in Example 4 was changed to 600 nm.

Subsequently, face masks and cleansing sheets were obtained by the same method as the method in Example 1 using this Nonwoven fabric for skin care products 17. The above-described evaluation was performed with respect to the obtained face masks and cleansing sheets. The constitutions and evaluation results of Nonwoven fabric for skin care products 17 are listed in Tables 3 and 4.

Example 18

Nonwoven fabric for skin care products 18 having a basis weight of 65 g/m² was obtained by the same method as the method in Example 8 except that the pressure of the hydroentanglement was changed to 13 MPa.

Subsequently, face masks and cleansing sheets were obtained by the same method as the method in Example 1 using this Nonwoven fabric for skin care products 18. The above-described evaluation was performed with respect to the obtained face masks and cleansing sheets. The constitutions and evaluation results of Nonwoven fabric for skin care products 18 are listed in Tables 3 and 4.

Comparative Example 1

After 52% by mass of the thermoplastic resin fiber (island component diameter: 230 nm) used in Example 2 and 48% by mass of a polyethylene terephthalate (PET) fiber (single fiber fineness: 1.6 dtex) were mixed and opened with a carding machine, web was formed with a cross-lap webber. The web was entangled by high pressure water flow under conditions of a pressure of 10 MPa and a flow rate of 1.0 m/min and dried at a drying temperature of 100° C. using a pin tenter to give a nonwoven fabric. The sea component was removed by treating the nonwoven fabric with a 1% sodium hydroxide aqueous solution under conditions of a temperature of 95° C., a bath ratio of 1:40, and a treatment time of 30 minutes to give Nonwoven fabric for skin care products 19 having a basis weight of 65 g/m² and including 30% by mass of the thermoplastic resin fiber (single fiber diameter: 230 nm) and 70% by mass of the polyethylene terephthalate (PET) fiber (single fiber fineness: 1.6 dtex). Here, the content of the thermoplastic resin fiber and the content of the PET fiber included in above-described Nonwoven fabric for skin care products 19 are the contents relative to the total mass of above-described Nonwoven fabric for skin care products 19 after removing the sea component.

Subsequently, face masks and cleansing sheets were obtained by the same method as the method in Example 1 using this Nonwoven fabric for skin care products 19. The above-described evaluation was performed with respect to the obtained face masks and cleansing sheets. The constitutions and evaluation results of Nonwoven fabric for skin care products 19 are listed in Tables 5 and 6.

Comparative Example 2

Nonwoven fabric for skin care products 20 having a basis weight of 65 g/m² was obtained by the same method as the method in Example 8 except that the rayon fiber (single fiber fineness: 1.4 dtex, strength at the time of a wet state: 1.1 cN/dtex, and fiber length: 38 mm) used in Example 8 was replaced by a lyocell fiber (single fiber fineness: 1.4 dtex, strength at the time of a wet state: 3.2 cN/dtex, and fiber length: 38 mm).

Subsequently, face masks and cleansing sheets were obtained by the same method as the method in Example 1 using this Nonwoven fabric for skin care products 20. The above-described evaluation was performed with respect to the obtained face masks and cleansing sheets. The constitutions and evaluation results of Nonwoven fabric for skin care products 20 are listed in Tables 5 and 6.

Comparative Example 3

Nonwoven fabric for skin care products 21 having a basis weight of 65 g/m² was obtained by the same method as the method in Example 8 except that the rayon fiber (single fiber fineness: 1.4 dtex, strength at the time of a wet state: 1.1 cN/dtex, and fiber length: 38 mm) used in Example 8 was replaced by a lyocell fiber (single fiber fineness: 1.25 dtex, strength at the time of a wet state: 2.4 cN/dtex, and fiber length: 38 mm).

Subsequently, face masks and cleansing sheets were obtained by the same method as the method in Example 1 using this Nonwoven fabric for skin care products 21. The above-described evaluation was performed with respect to the obtained face masks and cleansing sheets. The constitutions and evaluation results of Nonwoven fabric for skin care products 21 are listed in Tables 5 and 6.

Comparative Example 4

Nonwoven fabric for skin care products 22 having a basis weight of 65 g/m² was obtained by the same method as the method in Example 2 except that the content of the thermoplastic resin fiber (island component diameter: 230 nm) used in Example 2 was changed to 30% by mass, that the content of the rayon fiber (single fiber fineness: 1.4 dtex, strength at the time of a wet state: 1.1 cN/dtex, and fiber length: 38 mm) used in Example 2 was changed to 50% by mass, and that the content of the PET fiber (single fiber fineness: 1.6 dtex) used in Example 2 was changed to 20% by mass.

Subsequently, face masks and cleansing sheets were obtained by the same method as the method in Example 1 using this Nonwoven fabric for skin care products 22. The above-described evaluation was performed with respect to the obtained face masks and cleansing sheets. The constitutions and evaluation results of Nonwoven fabric for skin care products 22 are listed in Tables 5 and 6.

Comparative Example 5

Nonwoven fabric for skin care products 23 having a basis weight of 65 g/m² was obtained by the same method as the method in Example 8 except that the content of the thermoplastic resin fiber (single fiber diameter: 230 nm) used in Example 8 was changed to 65% by mass and that the content of the rayon fiber (single fiber fineness: 1.4 dtex, strength at the time of a wet state: 1.1 cN/dtex, and fiber length: 38 mm) used in Example 8 was changed to 35% by mass.

Subsequently, face masks and cleansing sheets were obtained by the same method as the method in Example 1 using this Nonwoven fabric for skin care products 23. The above-described evaluation was performed with respect to the obtained face masks and cleansing sheets. The constitutions and evaluation results of Nonwoven fabric for skin care products 23 are listed in Tables 5 and 6.

Comparative Example 6

Nonwoven fabric for skin care products 24 having a basis weight of 65 g/m² was obtained by the same method as the method in Example 8 except that the content ratio by mass of nylon 6 was changed to 80% by mass, that the content ratio by mass of the poly (L-lactic acid) was changed to 20% by mass with respect to the polymer alloy fiber in Example 8, and that the island component diameter of the thermoplastic resin fiber was changed to 1,000 nm.

Subsequently, face masks and cleansing sheets were obtained by the same method as the method in Example 1 using this Nonwoven fabric for skin care products 24. The above-described evaluation was performed with respect to the obtained face masks and cleansing sheets. The constitutions and evaluation results of Nonwoven fabric for skin care products 24 are listed in Tables 5 and 6.

Comparative Example 7

Nonwoven fabric for skin care products 25 having a basis weight of 65 g/m² was obtained by the same method as the method in Example 8 except that the content of the thermoplastic resin fiber (single fiber diameter: 230 nm) used in Example 8 was changed to 15% by mass and that the content of the rayon fiber (single fiber fineness: 1.4 dtex, strength at the time of a wet state: 1.1 cN/dtex, and fiber length: 38 mm) used in Example 8 was changed to 85% by mass.

Subsequently, face masks and cleansing sheets were obtained by the same method as the method in Example 1 using this Nonwoven fabric for skin care products 25. The above-described evaluation was performed with respect to the obtained face masks and cleansing sheets. The constitutions and evaluation results of Nonwoven fabric for skin care products 25 are listed in Tables 5 and 6.

Comparative Example 8

A nonwoven fabric for skin care products having a basis weight of 65 g/m² was obtained by the same method as the method in Example 8 except that the pressure of the hydroentanglement was changed to 7 MPa.

Subsequently, face masks and cleansing sheets were obtained by the same method as the method in Example 1 using this nonwoven fabric for skin care products. The above-described evaluation was performed with respect to the face masks and the cleansing sheets of this Example. The constitutions and evaluation results of Nonwoven fabric for skin care products 26 are listed in Tables 5 and 6.

Comparative Example 9

A nonwoven fabric for skin care products having a basis weight of 65 g/m² was obtained by the same method as the method in Example 8 except that the pressure of the hydroentanglement was changed to 18 MPa.

Subsequently, face masks and cleansing sheets were obtained by the same method as the method in Example 1 using this nonwoven fabric for skin care products. The above-described evaluation was performed with respect to the face masks and the cleansing sheets of this Example. The constitutions and evaluation results of Nonwoven fabric for skin care products 27 are listed in Tables 5 and 6.

As listed in Tables 1 to 6, the adhesion of the face mask and the wipeability of the cleansing sheet in Comparative Example 1 were inferior to the adhesion of the face masks and the wipeability of the cleansing sheets in Examples 1 to 18. The reason is presumed to be that the static coefficient of friction, followability, and softness at compression of Nonwoven fabric for skin care products 19 used for the face mask and cleansing sheet in Comparative Example 1 were inferior to the static coefficient of friction, followability, and softness at compression of Nonwoven fabrics for skin care products 1 to 18 used for the face masks and cleansing sheets in Examples 1 to 18.

The adhesion of the face masks and the wipeability of the cleansing sheets in Comparative Examples 2 and 3 were inferior to the adhesion of the face masks and the wipeability of the cleansing sheets in Examples 1 to 18. The reason is presumed to be that the static coefficient of friction, followability, and softness at compression of Nonwoven fabrics for skin care products 20 and 21 used for the face masks and cleansing sheets in Comparative Examples 2 and 3 were inferior to the static coefficient of friction, followability, and softness at compression of Nonwoven fabrics 1 to 18.

The adhesion of the face mask and the wipeability of the cleansing sheet in Comparative Example 4 were inferior to the adhesion of the face masks and the wipeability of the cleansing sheets in Examples 2 and 3. The reason is presumed to be that the static coefficient of friction, followability, and softness at compression of Nonwoven fabric for skin care products 22 used for the face mask and cleansing sheet in Comparative Example 4 were inferior to the static coefficient of friction, followability, liquid retention property, and softness at compression of Nonwoven fabrics for skin care products 2 and 3 used for the face masks and cleansing sheets in Comparative Examples 2 and 3.

The wipeability and handleability of the cleansing sheet in Comparative Example 5 were inferior the wipeability and handleability of the cleansing sheets in Examples 8 and 11 to 13. The reason is presumed to be that the content of the thermoplastic resin fiber included in Nonwoven fabric for skin care products 23 used for the cleansing sheet in Comparative Example 5 was higher than the contents of the thermoplastic resin fiber included in Nonwoven fabrics for skin care products 8 and 11 to 13.

The adhesion of the face mask and the wipeability of the cleansing sheet in Comparative Example 6 were inferior to the adhesion of the face masks and the wipeability of the cleansing sheets in Examples 4, 5 and, 8. The reason is presumed to be that the static coefficient of friction of Nonwoven fabric for skin care products 24 used for the face mask and cleansing sheet in Comparative Example 6 was inferior to the static coefficients of friction of Nonwoven fabrics for skin care products 4, 5 and, 8 used for the face masks and cleansing sheets in Examples 4, 5, and 8.

The adhesion of the face mask and the wipeability of the cleansing sheet in Comparative Example 7 were inferior to the adhesion of the face masks and the wipeability of the cleansing sheets in Examples 4, 5 and, 8. The reason is presumed to be that the content of the thermoplastic resin fiber included in Nonwoven fabric for skin care products 25 used for the face mask and the cleansing sheet in Comparative Example 7 was lower than the contents of the thermoplastic resin fiber included in Nonwoven fabrics for skin care products 4, 5, and 8.

The wipeability and handleability of the cleansing sheet in Comparative Example 8 were inferior to the wipeability and the handleability of the cleansing sheets in Examples 8, 15, 16, and 18. The reason is presumed to be that the density of Nonwoven fabric for skin care products 26 used for the cleansing sheet in Comparative Example 8 was lower than the densities of Nonwoven fabrics for skin care products 8, 15, 16, and 18.

The adhesion of the face mask and the wipeability of the cleansing sheet in Comparative Example 9 were inferior to the adhesion of the face masks and the wipeability of the cleansing sheets in Examples 8, 15, 16, and 18. The reason is presumed to be that the density of Nonwoven fabric for skin care products 27 used for the face mask and the cleansing sheet in Comparative Example 9 was higher than the densities of Nonwoven fabrics for skin care products 8, 15, 16, and 18 and that the followability and softness at compression of Nonwoven fabric for skin care products 27 were inferior to the followability and softness at compression of Nonwoven fabrics for skin care products 8, 15, 16, and 18.

Here, the adhesion of the face mask after 20 minutes and the wipeability of the cleansing sheet in Example 3 were superior to the adhesion of the face mask after 20 minutes and the wipeability of the cleansing sheet in Example 2. The reason is presumed to be that the sectional shape of the PET fiber included in Nonwoven fabric for skin care products 3 in Example 3 is the flat multi-leaf section, whereas the sectional shape of the PET fiber included in Nonwoven fabric for skin care products 2 in Example 2 is the circular section and thus that the static coefficient of friction, followability, liquid retention property, and softness at compression of Nonwoven fabric for skin care products 3 are superior to the static coefficient of friction, followability, liquid retention property, and softness at compression of Nonwoven fabric 2.

The adhesion of the face mask after 20 minutes and the wipeability of the cleansing sheet in Example 5 were superior to the adhesion of the face mask after 20 minutes and the wipeability of the cleansing sheet in Example 4. The reason is presumed to be that the static coefficient of friction, followability, liquid retention property, and softness at compression of Nonwoven fabric for skin care products 5 used for the face mask and the cleansing sheet in Example 5 were superior to the static coefficient of friction, followability, liquid retention property, and softness at compression of Nonwoven fabric for skin care products 4 in Example 4.

The followability of the face mask and the wipeability of the cleansing sheet in Example 8 were superior to the followability of the face masks and the wipeability of the cleansing sheets in Examples 6 and 7. The reason is presumed to be that the followability, liquid retention property, and softness at compression of Nonwoven fabric for skin care products 8 were superior to the followability, liquid retention property, and softness at compression of Nonwoven fabric for skin care products 6 and Nonwoven fabric for skin care products 7 used for the face masks and the cleansing sheets in Example 6 and Example 7.

The adhesion of the face mask after 20 minutes and the wipeability of the cleansing sheet in Example 8 were superior to the adhesion of the face mask after 20 minutes and the wipeability of the cleansing sheet in Example 1. The reason is presumed to be that the static coefficient of friction, followability, liquid retention property, and softness at compression of Nonwoven fabric for skin care products 8 are superior to the static coefficient of friction, followability, liquid retention property, and softness at compression of Nonwoven fabric for skin care products 1 used for the face mask and the cleansing sheet in Example 1.

The wipeability of the cleansing sheet in Example 8 was superior to the wipeability of the cleansing sheet in Example 9. The reason is presumed to be that the fiber length of the rayon fiber included in Nonwoven fabric for skin care products 8 is longer than the fiber length of the rayon fiber included in Nonwoven fabric for skin care products 9 used for the cleansing sheet in Example 9 and thus that a degree of entanglement of Nonwoven fabric for skin care products 8 is higher than that of Nonwoven fabric for skin care products 9, resulting in a higher strength at the time of a wet state of Nonwoven fabric for skin care products 8 than the strength at the time of a wet state of Nonwoven fabric for skin care products 9. The same applies to the assumption in which the wipeability of the cleansing sheet in Example 8 is superior to the wipeability of the cleansing sheet in Example 10.

The softness at compression of the face mask in Example 8 was superior to the softness at compression of the face mask in Example 10. The reason is presumed to be that Nonwoven fabric for skin care products 8 is a dry nonwoven fabric while Nonwoven fabric for skin care products 10 is a wet nonwoven fabric.

The adhesion and softness at compression of the face mask and the wipeability of the cleansing sheet in Example 8 were superior to the adhesion and softness at compression of the face mask and the wipeability of the cleansing sheet in Example 11. The reason is presumed to be that the content of the thermoplastic resin fiber included in Nonwoven fabric for skin care products 8 was higher than the content of the thermoplastic resin fiber included in Nonwoven fabrics for skin care products 11 used for the face mask and the cleansing sheet in Example 11.

The handleability of the cleansing sheet in Example 8 was superior to the handleability of the cleansing sheet in Example 12. The reason is presumed to be that the content of the thermoplastic resin fiber included in Nonwoven fabric for skin care products 8 was lower than the content of the thermoplastic resin fiber included in Nonwoven fabrics for skin care products 12 used for the cleansing sheet in Example 12.

The wipeability and handleability of the cleansing sheet in Example 8 were superior to the wipeability and handleability of the cleansing sheets in Examples 13 and 14. The reason is presumed to be that the content of the thermoplastic resin fiber included in Nonwoven fabric for skin care products 8 was lower than the contents of the thermoplastic resin fiber included in Nonwoven fabrics for skin care products 13 and 14 used for the cleansing sheet in Examples 13 and 14.

The wipeability and handleability of the cleansing sheet in Example 8 were superior to the wipeability and handleability of the cleansing sheet in Examples 15. The reason is presumed to be that the density of Nonwoven fabric for skin care products 8 was higher than the density of Nonwoven fabric for skin care products 15 used for the cleansing sheet in Examples 15.

The followability and softness at compression of the face mask in Example 8 were superior to the followability and softness at compression of the face mask in Example 16. The reason is presumed to be that the density of Nonwoven fabric for skin care products 8 was lower than the density of Nonwoven fabric for skin care products 16 used for the face mask in Examples 16.

The adhesion of the face mask after 20 minutes in Example 17 was superior to the adhesion of the face mask after 20 minutes in Example 4. The reason is presumed to be that the static coefficient of friction, followability, liquid retention property, and softness at compression of Nonwoven fabric for skin care products 17 used for the face mask in Example 17 were superior to the static coefficient of friction, followability, liquid retention property, and softness at compression of Nonwoven fabric for skin care products 4.

The followability and softness at compression of the face mask in Example 18 was superior to the followability and softness at compression of the face mask in Example 16. The reason is presumed to be that the density of Nonwoven fabric for skin care products 18 used for the face mask in Example 18 was lower than the density of Nonwoven fabric for skin care products 16 used for the cleansing sheet in Examples 16.

TABLE 1

| | | | Unit | Example 1 | Example 2 | Example 3 | Example 4 | Example 5 | Example 6 | Example 7 | Example 8 | Example 9 | Example 10 |
|---|---|---|---|---|---|---|---|---|---|---|---|---|---|
| Nonwoven fabric constitution | Thermoplastic resin fiber (A) | Material | — | PET | N6 | N6 | N6 | N6 | N6 | N6 | N6 | N6 | N6 |
| | | Single fiber diameter | nm | 230 | 230 | 230 | 700 | 300 | 230 | 230 | 230 | 230 | 230 |
| | | Content | % by mass | 30 | 30 | 30 | 30 | 30 | 30 | 30 | 30 | 30 | 30 |
| | Cellulose fiber (B) | Material | — | Rayon | Rayon | Rayon | Rayon | Rayon | Rayon | Rayon | Rayon | Rayon | Rayon |
| | | Single fiber fineness | dtex | 1.4 | 1.4 | 1.4 | 1.4 | 1.4 | 1.8 | 1.6 | 1.4 | 1.4 | 1.4 |
| | | Tensile strength | cN/dtex | 1.1 | 1.1 | 1.1 | 1.1 | 1.1 | 1.9 | 1.6 | 1.1 | 1.1 | 1.1 |
| | | Fiber length | mm | 38 | 38 | 38 | 38 | 38 | 38 | 38 | 38 | 32 | 15 |
| | | Content | % by mass | 70 | 55 | 55 | 70 | 70 | 70 | 70 | 70 | 70 | 70 |
| | Other fiber | Material | — | — | PET | PET | — | — | — | — | — | — | — |
| | | Single fiber fineness | dtex | — | 1.6 | 1.7 | — | — | — | — | — | — | — |
| | | Content | % by mass | — | 15 | 15 | — | — | — | — | — | — | — |
| | Content ratio by mass of A and B | | A/B | 0.43 | 0.55 | 0.55 | 0.43 | 0.43 | 0.43 | 0.43 | 0.43 | 0.43 | 0.43 |
| | Basis weight | | g/m² | 65 | 65 | 65 | 65 | 65 | 65 | 65 | 65 | 65 | 65 |
| | Thickness | | mm | 0.60 | 0.60 | 0.60 | 0.60 | 0.60 | 0.60 | 0.60 | 0.60 | 0.60 | 0.45 |
| | Density | | g/cm³ | 0.108 | 0.108 | 0.108 | 0.108 | 0.108 | 0.108 | 0.108 | 0.108 | 0.108 | 0.144 |

PET: Polyethylene terephthalate
N6: Nylon 6

TABLE 2

| | | Unit | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Physical property | Static coefficient of friction | — | 0.61 | 0.62 | 0.68 | 0.52 | 0.70 | 0.71 | 0.69 | 0.72 | 0.71 | 0.71 |
| | Followability (stress at 20% elongation) | N/25 mm | 3.0 | 4.0 | 3.9 | 3.4 | 2.7 | 3.6 | 3.0 | 2.5 | 2.2 | 2.0 |
| | Liquid retention property (Mass retention ratio of lotion) | % | 84 | 76 | 77 | 77 | 81 | 82 | 83 | 88 | 87 | 86 |

TABLE 2-continued

|  |  | Unit | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
|  | Softness at compression (WC value) | gf · cm/cm$^2$ | 0.62 | 0.45 | 0.61 | 0.56 | 0.66 | 0.58 | 0.64 | 0.71 | 0.65 | 0.37 |
| Monitoring evaluation | Adhesion immediately after use | — | A | A | A | A | A | A | A | A | A | A |
|  | Adhesion after 20 minutes | — | B | B | A | B | A | A | A | A | A | A |
|  | Followability | — | A | B | B | B | A | B | B | A | A | A |
|  | Difficulty in drying | — | A | B | B | B | B | A | A | A | A | A |
|  | Softness at compression | — | A | B | A | B | A | B | A | A | A | C |
|  | Wipeability | — | B | B | A | B | A | B | B | A | B | C |
|  | Handleability | — | A | A | A | A | A | A | A | A | C | C |
|  | Comprehensive evaluation | — | A | B | A | A | A | A | A | A | B | B |

TABLE 3

|  |  |  | Unit | Example 11 | Example 12 | Example 13 | Example 14 | Example 15 | Example 16 | Example 17 | Example 18 |
|---|---|---|---|---|---|---|---|---|---|---|---|
| Nonwoven fabric constitution | Thermoplastic resin fiber (A) | Material | — | N6 | N6 | N6 | N6 | N6 | N6 | N6 | N6 |
|  |  | Single fiber diameter | nm | 230 | 230 | 230 | 230 | 230 | 230 | 600 | 230 |
|  |  | Content | % by mass | 20 | 40 | 50 | 50 | 30 | 30 | 30 | 30 |
|  | Cellulose fiber (B) | Material | — | Rayon | Rayon | Rayon | Rayon | Rayon | Rayon | Rayon | Rayon |
|  |  | Single fiber fineness | dtex | 1.4 | 1.4 | 1.4 | 1.4 | 1.4 | 1.4 | 1.4 | 1.4 |
|  |  | Tensile strength | cN/dtex | 1.1 | 1.1 | 1.1 | 1.1 | 1.1 | 1.1 | 1.1 | 1.1 |
|  |  | Fiber length | mm | 38 | 38 | 38 | 38 | 38 | 38 | 38 | 38 |
|  |  | Content | % by mass | 80 | 60 | 50 | 35 | 70 | 70 | 70 | 70 |
|  | Other fiber | Material | — | — | — | — | PET | — | — | — | — |
|  |  | Single fiber fineness | dtex | — | — | — | 1.6 | — | — | — | — |
|  |  | Content | % by mass | — | — | — | 15 | — | — | — | — |
|  | Content ratio by mass of A and B | | A/B | 0.25 | 0.67 | 1.00 | 1.43 | 0.43 | 0.43 | 0.43 | 0.43 |
|  | Basis weight | | g/m$^2$ | 65 | 65 | 65 | 65 | 65 | 65 | 65 | 65 |
|  | Thickness | | mm | 0.60 | 0.60 | 0.60 | 0.60 | 0.80 | 0.42 | 0.60 | 0.47 |
|  | Density | | g/cm$^3$ | 0.108 | 0.108 | 0.108 | 0.108 | 0.081 | 0.155 | 0.108 | 0.138 |

PET: Polyethylene terephthalate
N6: Nylon 6

TABLE 4

|  |  | Unit | Example 11 | Example 12 | Example 13 | Example 14 | Example 15 | Example 16 | Example 17 | Example 18 |
|---|---|---|---|---|---|---|---|---|---|---|
| Physical property | Static coefficient of friction | — | 0.51 | 0.76 | 0.81 | 0.73 | 0.71 | 0.70 | 0.58 | 0.71 |
|  | Followability (stress at 20% elongation) | N/25 mm | 2.9 | 2.1 | 2.0 | 2.3 | 2.1 | 4.1 | 2.9 | 2.9 |
|  | Liquid retention property (Mass retention ratio of lotion) | % | 84 | 89 | 90 | 79 | 9 | 88 | 80 | 88 |

TABLE 4-continued

|  |  | Unit | Example 11 | Example 12 | Example 13 | Example 14 | Example 15 | Example 16 | Example 17 | Example 18 |
|---|---|---|---|---|---|---|---|---|---|---|
|  | Softness at compression (WC value) | gf·cm/cm² | 0.43 | 0.73 | 0.74 | 0.72 | 0.76 | 0.38 | 0.65 | 0.43 |
| Monitoring evaluation | Adhesion immediately after use | — | B | A | A | A | A | A | A | A |
|  | Adhesion after 20 minutes | — | B | A | A | A | A | A | A | A |
|  | Followability | — | A | A | A | A | A | B | A | A |
|  | Difficulty in drying | — | B | A | A | B | A | A | B | A |
|  | Softness at compression | — | B | A | A | A | A | C | A | B |
|  | Wipeability | — | B | A | B | B | C | A | B | A |
|  | Handleability | — | A | C | C | B | C | A | A | A |
|  | Comprehensive evaluation | — | B | B | B | A | B | B | A | A |

TABLE 5

|  |  |  | Unit | Comparative Example 1 | Comparative Example 2 | Comparative Example 3 | Comparative Example 4 | Comparative Example 5 |
|---|---|---|---|---|---|---|---|---|
| Nonwoven fabric constitution | Thermoplastic resin fiber (A) | Material | — | N6 | N6 | N6 | N6 | N6 |
|  |  | Single fiber diameter | nm | 230 | 230 | 230 | 230 | 230 |
|  |  | Content | % by mass | 30 | 30 | 30 | 30 | 65 |
|  | Cellulose fiber (B) | Material | — | — | Lyocell | Lyocell | Rayon | Rayon |
|  |  | Single fiber fineness | dtex | — | 1.4 | 1.25 | 1.4 | 1.4 |
|  |  | Tensile strength | cN/dtex | — | 3.2 | 2.4 | 1.1 | 1.1 |
|  |  | Fiber length | mm | — | 38 | 38 | 38 | 38 |
|  |  | Content | % by mass | — | 70 | 70 | 50 | 35 |
|  | Other fiber | Material | — | PET | — | — | PET | — |
|  |  | Single fiber fineness | dtex | 1.6 | — | — | 1.6 | — |
|  |  | Content | % by mass | 70 | — | — | 20 | — |
|  | Content ratio by mass of A and B | | A/B | — | 0.43 | 0.43 | 0.60 | 1.86 |
|  | Basis weight | | g/m² | 65 | 65 | 65 | 65 | 65 |
|  | Thickness | | mm | 0.60 | 0.60 | 0.60 | 0.60 | 0.60 |
|  | Density | | g/cm³ | 0.108 | 0.108 | 0.108 | 0.108 | 0.108 |

|  |  |  | Unit | Comparative Example 6 | Comparative Example 7 | Comparative Example 8 | Comparative Example 9 |
|---|---|---|---|---|---|---|---|
| Nonwoven fabric constitution | Thermoplastic resin fiber (A) | Material | — | N6 | N6 | N6 | N6 |
|  |  | Single fiber diameter | nm | 1000 | 230 | 230 | 230 |
|  |  | Content | % by mass | 30 | 15 | 30 | 30 |
|  | Cellulose fiber (B) | Material | — | Rayon | Rayon | Rayon | Rayon |
|  |  | Single fiber fineness | dtex | 1.4 | 1.4 | 1.4 | 1.4 |
|  |  | Tensile strength | cN/dtex | 1.1 | 1.1 | 1.1 | 1.1 |
|  |  | Fiber length | mm | 38 | 38 | 38 | 38 |
|  |  | Content | % by mass | 70 | 85 | 70 | 70 |

TABLE 5-continued

|  |  |  |  |  |  |  |
|---|---|---|---|---|---|---|
| Other fiber | Material | — | — | — | — | — |
|  | Single fiber fineness | dtex | — | — | — | — |
|  | Content | % by mass | — | — | — | — |
| Content ratio by mass of A and B | | A/B | 0.43 | 0.18 | 0.43 | 0.43 |
| Basis weight | | g/m² | 65 | 65 | 65 | 65 |
| Thickness | | mm | 0.60 | 0.60 | 0.90 | 0.38 |
| Density | | g/cm³ | 0.108 | 0.108 | 0.072 | 0.171 |

PET: Polyethylene terephthalate
N6: Nylon 6

TABLE 6

|  |  | Unit | Comparative Example 1 | Comparative Example 2 | Comparative Example 3 | Comparative Example 4 | Comparative Example 5 |
|---|---|---|---|---|---|---|---|
| Physical property | Static coefficient of friction | — | 0.44 | 0.47 | 0.48 | 0.48 | 0.85 |
|  | Followability (stress at 20% elongation) | N/25 mm | 6.4 | 5.5 | 5.0 | 5.2 | 1.5 |
|  | Liquid retention property (Mass retention ratio of lotion) | % | 67 | 77 | 76 | 73 | 91 |
|  | Softness at compression (WC value) | gf · cm/cm² | 0.26 | 0.36 | 0.35 | 0.38 | 0.75 |
| Monitoring evaluation | Adhesion immediately after use | — | C | B | B | B | A |
|  | Adhesion after 20 minutes | — | D | C | C | C | A |
|  | Followability | — | D | D | C | D | A |
|  | Difficulty in drying | — | D | B | B | D | A |
|  | Softness at compression | — | D | C | C | C | A |
|  | Wipeability | — | D | C | C | C | D |
|  | Handleability | — | A | A | A | A | D |
|  | Comprehensive evaluation | — | D | D | C | D | D |

|  |  | Unit | Comparative Example 6 | Comparative Example 7 | Comparative Example 8 | Comparative Example 9 |
|---|---|---|---|---|---|---|
| Physical property | Static coefficient of friction | — | 0.35 | 0.45 | 0.71 | 0.70 |
|  | Followability (stress at 20% elongation) | N/25 mm | 4.0 | 3.2 | 1.6 | 5.3 |
|  | Liquid retention property (Mass retention ratio of lotion) | % | 75 | 77 | 88 | 88 |
|  | Softness at compression (WC value) | gf · cm/cm² | 0.57 | 0.37 | 0.83 | 0.27 |
| Monitoring evaluation | Adhesion immediately after use | — | B | B | A | B |
|  | Adhesion after 20 minutes | — | C | C | A | C |
|  | Followability | — | C | B | A | D |
|  | Difficulty in drying | — | B | B | A | A |
|  | Softness at compression | — | B | C | A | D |

TABLE 6-continued

| | | | | | |
|---|---|---|---|---|---|
| Wipeability | — | C | C | D | C |
| Handleability | — | A | A | D | A |
| Comprehensive evaluation | — | C | C | C | C |

The invention claimed is:

1. A nonwoven fabric for skin care products, the nonwoven skin care fabric comprising:
   a thermoplastic resin fiber having a single fiber diameter of 50 nm or more and 800 nm or less;
   a cellulose fiber, wherein
   a tensile strength of the cellulose fiber measured in accordance with JIS L 1015:2010 8.7.2 is 1.9 cN/dtex or less,
   a content ratio by mass of the thermoplastic resin fiber and the cellulose fiber is 0.23 to 1.50, and
   a density of the nonwoven skin care fabric is 0.08 g/cm$^3$ to 0.16 g/cm$^3$,
   wherein the nonwoven fabric further comprises a polyethylene terephthalate fiber having a single fiber fineness of 1.6 dtex or more, a sectional shape of the plyethylene terephthalate fiber being a flat section.

2. The nonwoven skin care fabric according to claim 1, wherein the thermoplastic resin fiber is a polyamide fiber.

3. The nonwoven skin care fabric according to claim 1, wherein the cellulose fiber is rayon.

4. The nonwoven skin care fabric according to claim 1, wherein a fiber length of the cellulose fiber is 35 mm or more.

5. The nonwoven skin care fabric according to claim 1, wherein the density is 0.08 g/cm$^3$ to 0.14 g/cm$^3$.

6. A face mask comprising the nonwoven skin care fabric according to claim 1.

7. A cleansing sheet comprising the nonwoven skin care fabric according to claim 1.

* * * * *